US009283558B2

(12) United States Patent
Ono et al.

(10) Patent No.: US 9,283,558 B2
(45) Date of Patent: Mar. 15, 2016

(54) FLUID HANDLING DEVICE

(71) Applicant: Enplas Corporation, Saitama (JP)

(72) Inventors: Koichi Ono, Saitama (JP); Ken Kitamoto, Saitama (JP)

(73) Assignee: Enplas Corporation, Saitama (JP)

(*) Notice: Subject to any disclaimer, the term of this patent is extended or adjusted under 35 U.S.C. 154(b) by 0 days.

(21) Appl. No.: 14/722,604

(22) Filed: May 27, 2015

(65) Prior Publication Data

US 2015/0343441 A1 Dec. 3, 2015

(30) Foreign Application Priority Data

May 27, 2014 (JP) ................................ 2014-109084

(51) Int. Cl.

| | |
|---|---|
| ***G01N 15/06*** | (2006.01) |
| ***G01N 33/00*** | (2006.01) |
| ***G01N 33/48*** | (2006.01) |
| ***B01L 3/00*** | (2006.01) |

(52) U.S. Cl.

CPC ....... *B01L 3/502707* (2013.01); *B01L 3/50273* (2013.01); *B01L 2200/12* (2013.01); *B01L 2300/0887* (2013.01); *B01L 2300/14* (2013.01)

(58) Field of Classification Search

CPC ........ G01N 15/06; G01N 33/00; G01N 33/48

USPC ............. 422/68.1, 81, 502, 503, 504; 436/43, 436/174, 180

See application file for complete search history.

(56) References Cited

U.S. PATENT DOCUMENTS

| | | | | |
|---|---|---|---|---|
| 4,273,639 | A * | 6/1981 | Gottermeier | 204/416 |
| 5,376,252 | A * | 12/1994 | Ekstrom et al. | 204/603 |
| 5,516,500 | A * | 5/1996 | Liu et al. | 423/446 |
| 5,554,415 | A * | 9/1996 | Turchan et al. | 427/248.1 |
| 5,595,712 | A * | 1/1997 | Harbster et al. | 422/129 |
| 5,620,754 | A * | 4/1997 | Turchan et al. | 427/554 |
| 5,658,413 | A * | 8/1997 | Kaltenbach et al. | 156/272.8 |
| 6,437,551 | B1 | 8/2002 | Krulevitch et al. | |
| 6,805,431 | B2 * | 10/2004 | Anderson et al. | 347/64 |
| 6,939,451 | B2 | 9/2005 | Zhao et al. | |
| 6,967,149 | B2 * | 11/2005 | Meyer et al. | 438/455 |
| 7,417,418 | B1 | 8/2008 | Ayliffe | |
| 7,595,004 | B2 * | 9/2009 | Giovanola et al. | 216/27 |

OTHER PUBLICATIONS

Extended European Search Report for EP 15167594.9 dated Oct. 12, 2015.

* cited by examiner

*Primary Examiner* — Brian J Sines

(74) *Attorney, Agent, or Firm* — Brundidge & Stanger, P.C.

(57) ABSTRACT

A fluid handling device includes a substrate, a film, and a conductive layer. The substrate includes a first through-hole, and a second through-hole. The conductive layer is disposed on one surface of the film to extend in a first area, a second area and a third area of the film. The substrate includes a first surface and a second surface facing away from the first surface. The first area is bonded to the first surface of the substrate such that a housing part is formed by closing one opening of the first through-hole, and such that a part of the conductive layer is exposed to the inside of the housing part. The second area is disposed inside the second through-hole, and the third area is bonded to the second surface of the substrate such that a part of the conductive layer is exposed to the outside.

6 Claims, 9 Drawing Sheets

FLUID HANDLING DEVICE

CROSS REFERENCE TO RELATED APPLICATIONS

This application is entitled to and claims the benefit of Japanese Patent Application No. 2014-109084, filed on May 27, 2014, the disclosure of which including the specification, drawings and abstract is incorporated herein by reference in its entirety.

1. Technical Field

The present invention relates to a fluid handling device for use in analyzing and processing liquid samples.

2. Background Art

In recent years, in the fields of science and medicine such as biochemistry and analytical chemistry, microanalysis systems have been used for high precision, high speed analysis of smaller amounts of materials such as protein and nucleic acids (e.g., DNA). Microanalysis systems can advantageously perform analysis with smaller amounts of reagents or samples and therefore are expected in various applications such as laboratory tests, food tests, and environment tests.

One example of the microanalysis systems is a system that analyzes a liquid sample using a microchannel chip having a fine channel (e.g., see PTL 1).

FIG. 1A is a plan view of microchannel chip 10 disclosed in PTL 1, and FIG. 1B is a sectional view taken along line B-B in FIG. 1A. As illustrated in FIG. 1A, microchannel chip 10 includes substrate 18 having a groove and four through-holes, and plate 20 made of glass or resin and having four electrically conductive layers (hereinafter also referred to as "conductive layer") 28 disposed on one surface thereof. Two of the four through-holes are in communication with both ends of the groove. The opening of the groove is closed by plate 20 to form microchannel (channel) 14. In addition, the openings, on the side of the opening of the groove, of the four through-holes are closed by plate 20 to form four reservoirs 26. The area of plate 20 is larger than that of substrate 18. Electrically conductive layer 28 is disposed on plate 20 with one end exposed to the inside of reservoir 26 and the other end exposed to the outside at a position outward from the outer edge of substrate 18.

The other end, exposed to the outside, of electrically conductive layer 28 of microchannel chip 10 is connected to a measurement device or the like via a connector (not illustrated). Microchannel chip 10 may be used for various types of analysis and processing of liquid samples.

CITATION LIST

Patent Literature

PTL 1: U.S. Pat. No. 6,939,451

SUMMARY OF INVENTION

Technical Problem

In microchannel chip 10 of PTL 1, the other end of electrically conductive layer 28 to be connected to a connector is disposed on plate 20 having sufficient strength at a position outward from the edge of substrate 18. Therefore, when the connector is pressed against electrically conductive layer 28, it is possible to connect the connector with a sufficient contact pressure. On the other hand, from the viewpoint of reduction in size and in manufacturing costs, a film may be desired in place of plate 20. In this case, since the film is undesirably deformed when the connector is brought into contact with electrically conductive layer 28, a sufficient contact pressure cannot be secured between the connector and electrically conductive layer 28.

An object of the present invention is to provide a fluid handling device that may be manufactured by bonding a film on which a conductive layer is formed to one surface thereof on a substrate in which a through-hole or a recess is formed, wherein a connector of a measurement device or the like can be connected to the conductive layer with a sufficient contact pressure even when the connector is pressed against the conductive layer provided on the film.

Solution to Problem

In order to achieve the above-described object, a fluid handling device of the present invention includes: a substrate including a first through-hole or a recess, and a second through-hole; a film including a first area, a second area disposed adjacent to the first area, and a third area disposed adjacent to the second area; and a conductive layer disposed on one surface of the film to extend in the first area, the second area and the third area to conduct electricity or heat, wherein: the substrate includes a first surface and a second surface facing away from the first surface, the first area of the film is bonded to the first surface of the substrate such that a housing part capable of housing liquid is formed by closing one opening of the first through-hole or an opening of the recess, and such that a part of the conductive layer is exposed to an inside of the housing part, the second area of the film is disposed inside the second through-hole, and the third area of the film is bonded to the second surface of the substrate such that a part of the conductive layer is exposed to an outside.

Advantageous Effects of Invention

According to the present invention, while the fluid handling device may be manufactured by bonding a film on which a conductive layer is formed on one surface thereof to a substrate in which a through-hole or a recess is formed, it is possible to connect a connector of a measurement device or the like to the conductive layer with a sufficient contact pressure even when the connector is pressed against the conductive layer provided on the film. Therefore, the fluid handling device according to the present invention can be properly installed for example in a measurement device having an insertion type connector, to thereby enable precise measurement to be performed for smaller amounts of material.

DESCRIPTION OF EMBODIMENTS

In the following, embodiments of the present invention will be described in detail with reference to the accompanying drawings. In the following description, a microchip and a microchannel chip will be described as typical examples of the fluid handling device according to the present invention.

Embodiment 1

In Embodiment 1, microchip 100 capable of heating liquids such as reagent and liquid sample will be described.

(Configuration of Microchip)

Figure 2A:
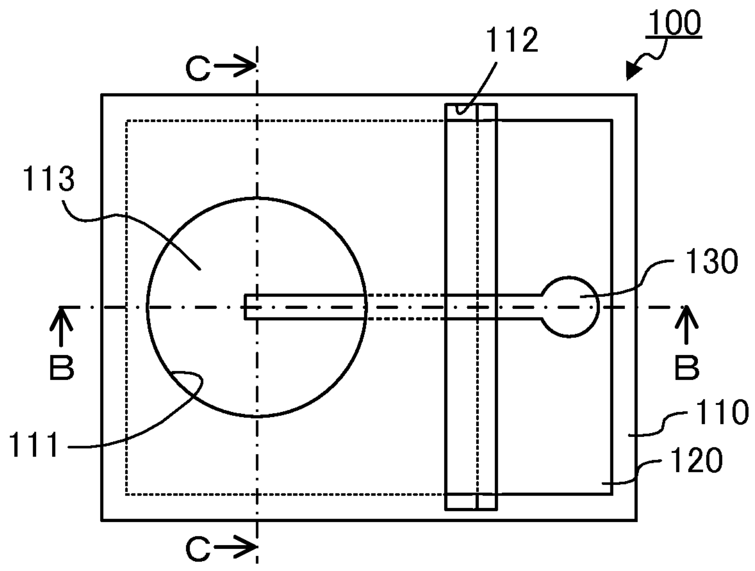
FIGS. 2A to 2C illustrate a configuration of a microchip according to Embodiment 1.
Figure 2B:
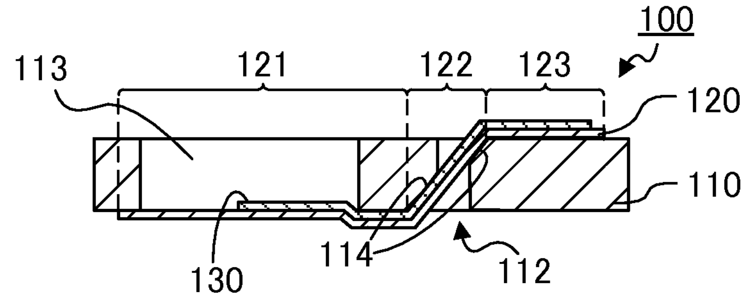
Figure 2C:
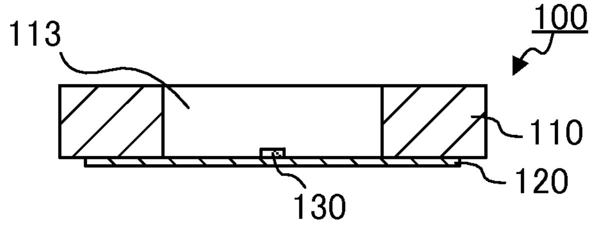
Figure 3A:
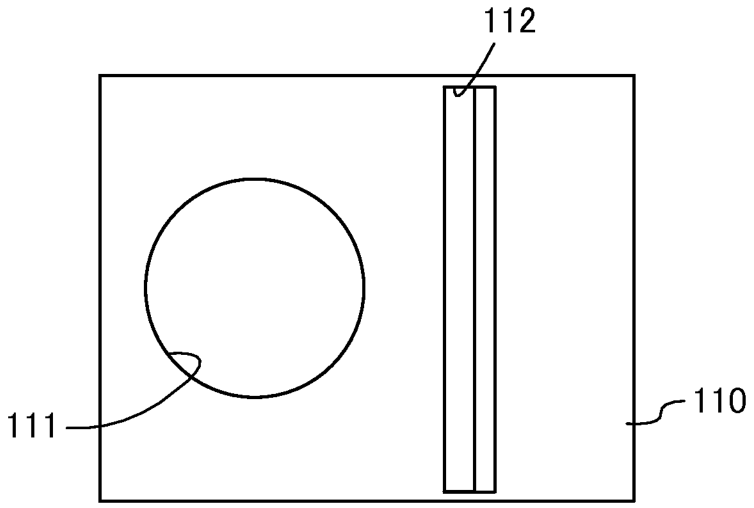
FIG. 3A is a plan view of a substrate.
Figure 3B:
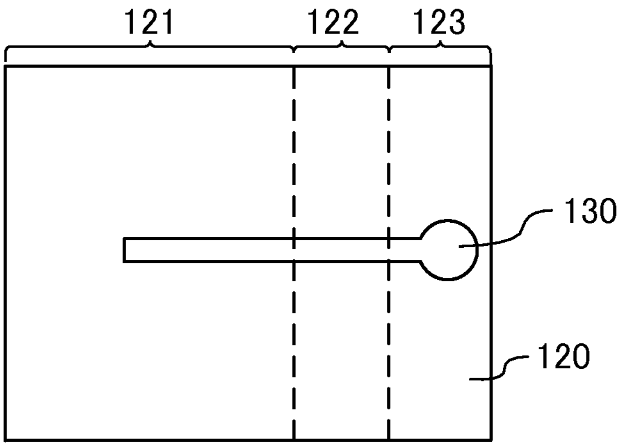
FIG. 3B is a plan view of a film on which a conductive layer is formed.

FIGS. 2A to 2C and 3A and 3B illustrate a configuration of microchip 100 according to Embodiment 1 of the present invention. FIG. 2A is a plan view of microchip 100, FIG. 2B is a sectional view taken along line B-B illustrated in FIG. 2A, and FIG. 2C is a sectional view taken along line C-C illustrated in FIG. 2A. FIG. 3A is a plan view of substrate 110, and FIG. 3B is a plan view of film 120 on which conductive layer 130 is formed.

As illustrated in FIGS. 2A to 2C, microchip 100 is a plate-like device having housing part 113. Microchip 100 includes substrate 110, film 120, and conductive layer 130.

Substrate 110 is a transparent substantially rectangular member, and includes first through-hole 111 and second through-hole 112. First through-hole 111 and second through-hole 112 open at both surfaces of substrate 110. One opening of first through-hole 111 is closed by film 120 to allow first through-hole 111 to function as housing part 113 capable of housing therein liquid. The shape and the size of first through-hole 111 are not particularly limited and may be appropriately set depending on applications. For example, first through-hole 111 has a substantially columnar shape with a diameter of 0.1 to 10 mm.

As illustrated in FIG. 2B, second through-hole 112 is a through-hole for disposing therein a part of film 120. The shape and the size of second through-hole 112 are not particularly limited insofar as second through-hole 112 can pass through film 120 without causing excessive stress. From the viewpoint of allowing film 120 to be passed through easily at the time of manufacturing, an inclining surface 114 may be formed, in at least one opening of second through-hole 112, to be away from housing part 113 (first through-hole 111) as being away from one surface (rear side) toward the other surface (front side) of substrate 110. In the present embodiment, inclining surface 114 is formed at each opening of second through-hole 112. In the longitudinal direction of conductive layer 130, the width of the opening of second through-hole 112 is, for example, about 1 to 2 mm.

The size and the thickness of substrate 110 are not particularly limited and can be appropriately set depending on applications. For example, the size of substrate 110 is 10 mm×20 mm, and the thickness of substrate 110 is 1 to 10 mm. The material for substrate 110 is not particularly limited and can be appropriately selected from known resins and glass depending on applications. Examples of the material for substrate 110 include polyethylene terephthalate, polycarbonate, polymethylmethacrylate, vinyl chloride, polypropylene, polyether, and polyethylene.

Film 120 is a transparent substantially rectangular resin film. As illustrated in FIG. 3B, film 120 includes first area 121, second area 122 disposed adjacent to first area 121, and third area disposed adjacent to second area 122. As described above, film 120 closes one opening of first through-hole 111 of substrate 110 to form housing part 113 capable of housing therein liquid. First area 121 of film 120 is bonded to one surface (rear side surface) of substrate 110 so as to close one opening of first through-hole 111, and third area 123 of film 120 is bonded to the other surface (front side surface) of substrate 110. Second area 122 of film 120 is disposed inside second through-hole 112. The method of bonding film 120 to substrate 110 is not particularly limited. However, from the viewpoint of preventing a liquid sample from leaking to the outside when the liquid sample is introduced into housing part 113, film 120 is bonded to substrate 110 such that no gap occurs between them. For example, film 120 is bonded to substrate 110 by means of laser welding, thermocompression bonding, adhesion by an adhesive, or the like.

The thickness of film 120 is not particularly limited insofar as the strength required for housing part 113 can be secured, and insofar as second area 122 of film 120 can be disposed inside second through-hole 112. For example, the thickness of film 120 is about 100 μm.

The material for film 120 is typically resin but is not particularly limited insofar as the material is flexible. Examples of resins as the material for film 120 include polyethylene terephthalate, polycarbonate, polyolefins, acrylic resins, and cycloolefin polymer (COP). From the viewpoint of enhancing the adhesion between substrate 110 and film 120, the material for film 120 is preferably the same as the material for substrate 110.

As illustrated in FIG. 3B, conductive layer 130 is a thermally or electrically conductive layer disposed on one surface of film 120 to extend in first area 121, second area 122 and third area 123. For example, conductive layer 130 is a thin metal film, a conductive ink layer (e.g., carbon ink layer), or the like. As illustrated in FIG. 2B, conductive layer 130 disposed on first area 121 of film 120 is disposed on one surface side (rear side) of substrate 110 such that a part of conductive layer 130 is exposed to the inside of housing part 113. Conductive layer 130 disposed on third area 123 of film 120 is disposed on the other surface side (front side) of substrate 110 such that conductive layer 130 is exposed to the outside. Conductive layer 130 may be used as an electrode, an electrothermal heater, a pH, temperature or flow rate sensor, an electrochemical detector, or the like. In the present embodiment, conductive layer 130 may be used as an electrothermal heater.

The shape and thickness of conductive layer 130 are not particularly limited insofar as conductive layer 130 can conduct heat or electricity enough to allow measurement, processing or the like of a liquid sample, and may be appropriately set depending on applications. For example, the width of conductive layer 130 is about 0.1 to 1 mm, and the thickness of conductive layer 130 is about 10 μm.

(Method of Manufacturing Microchip)

Next, a method of manufacturing microchip 100 according to Embodiment 1 will be described with reference to FIGS. 4A to 4C. Microchip 100 may be manufactured through the steps described below.

Figure 4A:
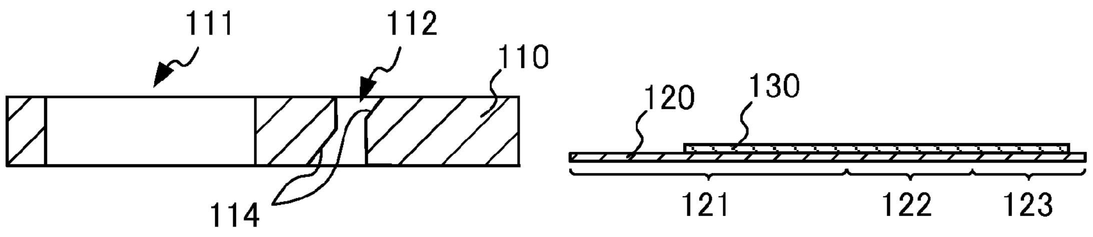
FIGS. 4A to 4C are explanatory sectional views of manufacturing steps of the microchip according to Embodiment 1.
Figure 4B:
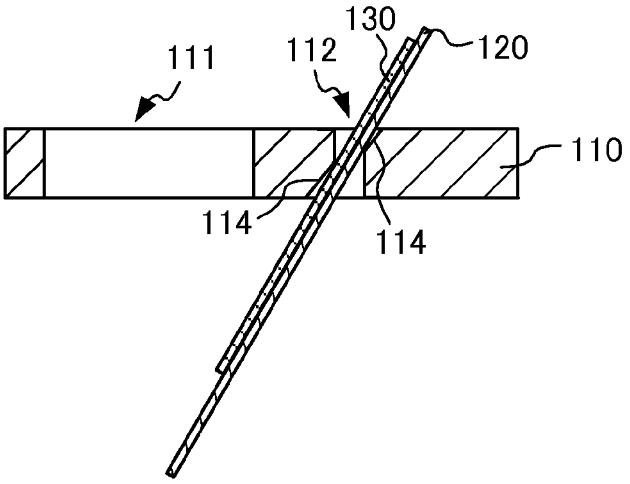
Figure 4C:
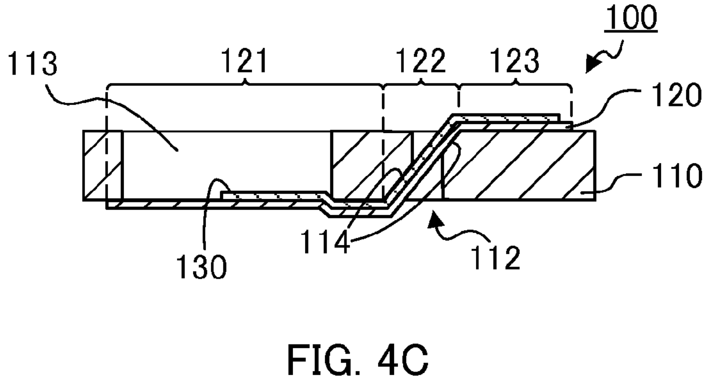

FIGS. 4A to 4C are explanatory sectional views of the method of manufacturing microchip 100 according to Embodiment 1. First, as illustrated in FIG. 4A, substrate 110, and film 120 on which conductive layer 130 is formed are provided. Substrate 110 has first through-hole 111 and second through-hole 112 formed therein. The method of forming first through-hole 111 and second through-hole 112 in substrate 110 is not particularly limited. For example, first through-hole 111 and second through-hole 112 may be formed by metal molding or lithography. The method of forming conductive layer 130 is not particularly limited. Conductive layer 130 may be formed, for example, by screen printing of conductive paste.

Next, as illustrated in FIG. 4B, film 120 on which conductive layer 130 is formed is passed through the inside of second through-hole 112 of substrate 110. Then, as illustrated in FIG. 4C, film 120 is bonded to both surfaces of substrate 110 by thermocompression to bond film 120 to substrate 110. Thus, housing part 113 is formed. In addition, one end of conductive layer 130 is exposed to the inside of housing part 113 on the rear side of substrate 110, and the other end of conductive layer 130 is exposed to the outside on the front side of substrate 110. Through the above-described steps, microchip 100 according to the present embodiment can be manufactured.

In microchip 100 thus manufactured, film 120 that lines the other end of conductive layer 130 is bonded to substrate 110. Therefore, it is possible to connect the other end of conductive layer 130 to a heater with a sufficient contact pressure, as described later.

Known conventional methods for exposing one end of the conductive layer to the inside of the housing part while exposing the other end of the conductive layer to the outside include forming conductive layers on both surfaces of the film and connecting the conductive layers via through-hole interconnection. In contrast, according to the present invention, while conductive layer 130 is formed only on one surface of film 120, one end of conductive layer 130 can be exposed to the inside of housing part 113, and the other end of conductive layer 130 can be exposed to the outside. Accordingly, microchip 100 may be manufactured at low costs without using duplex printing.

(Method of Using Microchip)

Next, a method of using microchip 100 according to Embodiment 1 will be described with reference to FIG. 5.

Figure 1A:
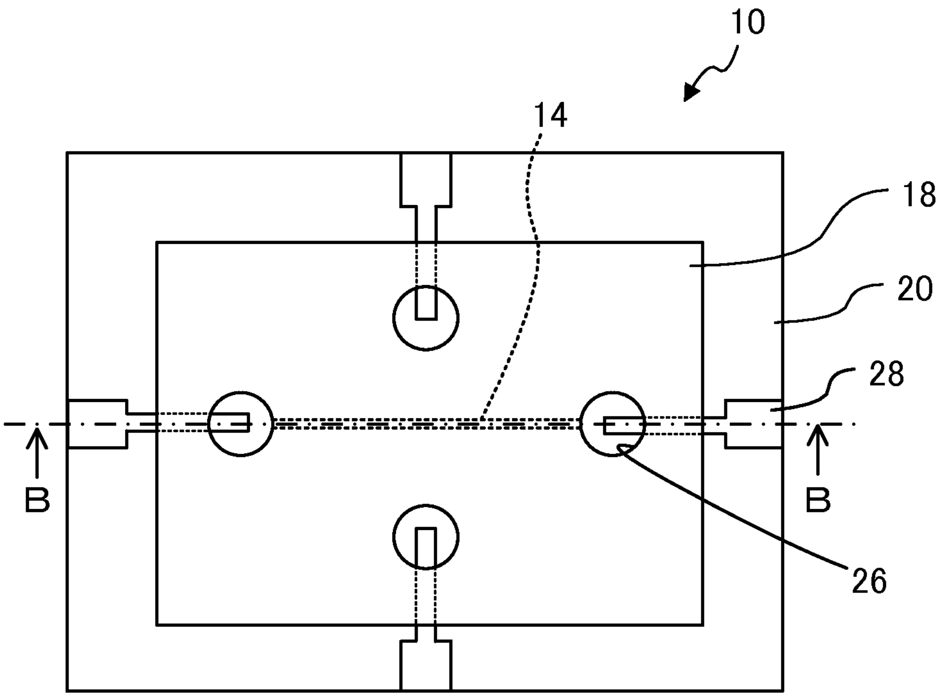
FIGS. 1A and 1B illustrate a configuration of a microchannel chip disclosed in PTL 1.
Figure 1B:
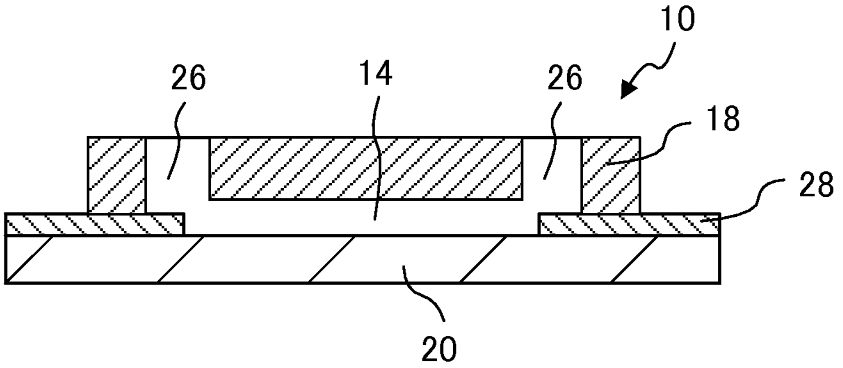
Figure 5:
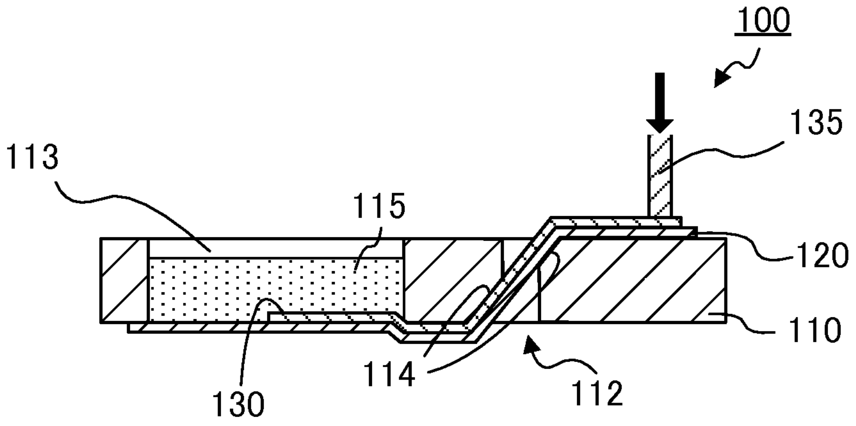
FIG. 5 is an explanatory drawing of a mode in which the microchip according to Embodiment 1 is used.

FIG. 5 is an explanatory drawing of a mode in which microchip 100 according to Embodiment 1 is used. As illustrated in FIG. 5, liquid 115 such as a reagent or a liquid sample is supplied to housing part 113 of microchip 100. Heater 135 is pressed against conductive layer 130. Conductive layer 130 is disposed on substrate 110 through film 120, and thus heater 135 can be connected to conductive layer 130 with a sufficient contact pressure. Since conductive layer 130 and heater 135 can be thus connected to each other at a position inward from the outer edge of substrate 110, microchip 100 can be reduced in size (see FIGS. 1B and 5 for comparison). Further, when heater 135 is heated in this state, it is possible to heat liquid 115 inside housing part 113 through conductive layer 130.

(Effect)

As described above, in microchip 100 according to Embodiment 1, it is possible to dispose conductive layer 130 on both sides of substrate 110 through second through-hole 112. Heater 135 and conductive layer 130 can contact each other on substrate 110 in a stable state. Therefore, conductive layer 130 and heater 135 may be connected to each other with a sufficient contact pressure. In addition to a heater, microchip 100 according to Embodiment 1 can also be properly installed for example in a measurement device having an insertion type connector, to thereby enable precise measurement, processing, or the like to be performed for smaller amounts of materials.

It is noted that while conductive layer 130 is used as a heater for heat treatment in the present embodiment, the application of the conductive layer is not limited to a heater for heat treatment.

In addition, the shape of the substrate is not limited to the shape illustrated in FIGS. 3A and 4A, either.

Figure 6A:
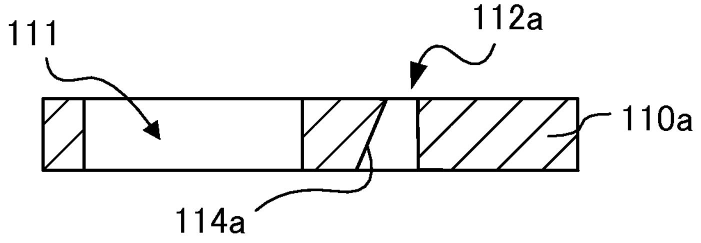
FIG. 6A is a sectional view of a substrate according to a first modification of Embodiment 1.
Figure 6B:
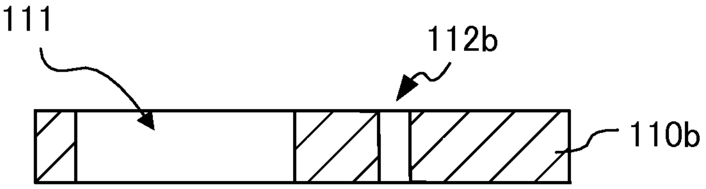
FIG. 6B is a sectional view of a substrate according to a second modification of Embodiment 1.
Figure 6C:
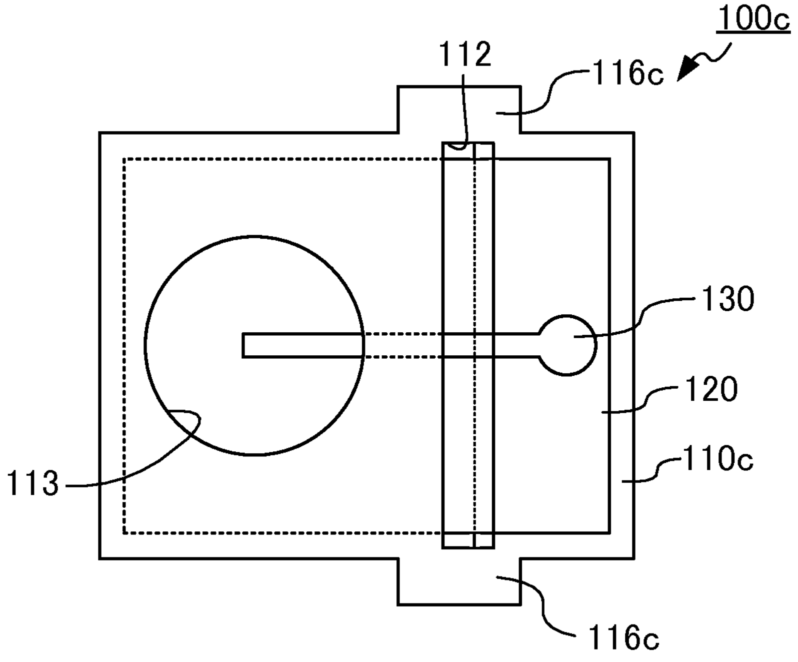
FIG. 6C is a plan view of a microchip according to a third modification of Embodiment 1.
Figure 7A:
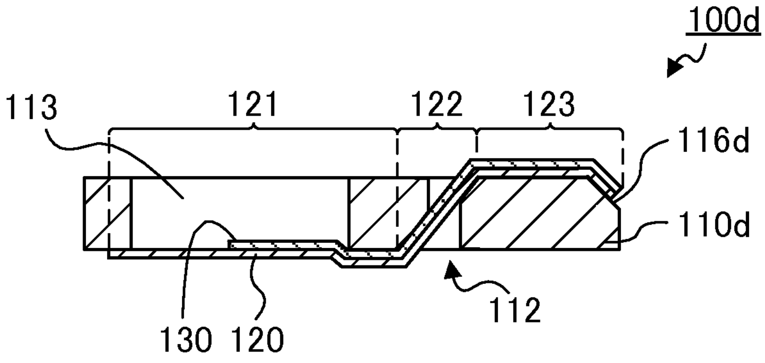
FIG. 7A is a sectional view illustrating a configuration of a microchip according to a fourth modification of Embodiment 1.

FIG. 6A is a sectional view of substrate **110*a* according to a first modification of Embodiment 1, FIG. 6B is a sectional view of substrate 110*b* according to a second modification of Embodiment 1, and FIG. 6C is a plan view illustrating the configuration of microchip 100*c* according to a third modification of Embodiment 1. FIG. 7A is a sectional view illustrating the configuration of microchip 100*d* according to a fourth modification of Embodiment 1, and FIG. 7B is a sectional view illustrating the configuration of microchip 100*e*** according to a fifth modification of Embodiment 1.

As illustrated in FIG. 6A, second through-hole **112*a* may have one inclining surface 114*a* to be away from first through-hole 111 (housing part 113) as being away from one surface (rear side) toward the other surface (front side) of substrate 110*a*. In addition, as illustrated in FIG. 6B, second through-hole 112*b*** does not need to have an inclining surface.

As illustrated in FIG. 6C, substrate **110*c* may have reinforcing parts 116*c* for reinforcing substrate 110*c* at positions facing the end portions of film 120 inside second through-hole 112. The shape and size of reinforcing part 116*c* are not particularly limited insofar as reinforcing part 116*c* can reinforce the periphery of second through-hole 112**.

Figure 7B:
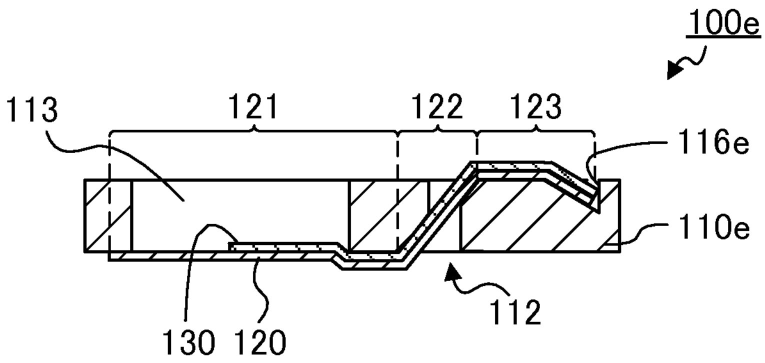
FIG. 7B is a sectional view illustrating a configuration of a microchip according to a fifth modification of Embodiment 1.

As illustrated in FIGS. 7A and 7B, a recess for housing the end portion in third area 123 of film 120 may be formed at the other surface of substrate 110. In microchip **100*d* according to the fourth modification illustrated in FIG. 7A, recess (cutout) 116*d* for housing the end portion in third area 123 of film 120 is formed at the end portion of the other surface of substrate 110*d*. In microchip 100*e* according to the fifth modification illustrated in FIG. 7B, recess 116*e* for housing the end portion in third area 123 of film 120 is formed at the other surface of substrate 110*e***.

The description of the present embodiment has been directed to microchip 100 having housing part 113 formed by closing the opening of first through-hole 111 of substrate 110 with film 120. However, substrate 110 may have a recess that functions as housing part 113 in place of first through-hole 111.

Figure 8A:
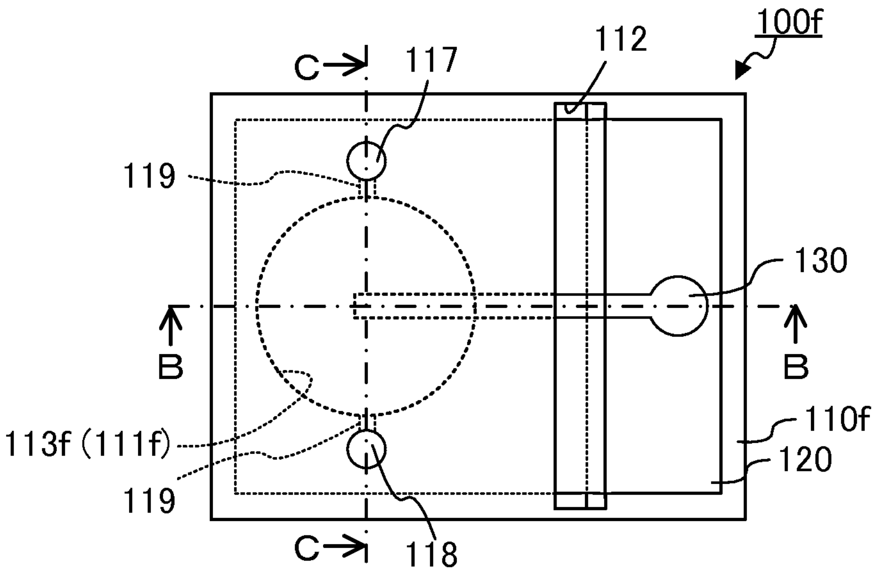
FIGS. 8A to 8C illustrate a configuration of a microchip according to a sixth modification of Embodiment 1.
Figure 8B:
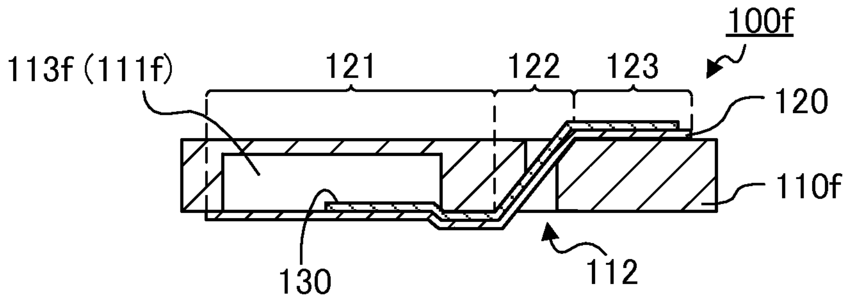
Figure 8C:
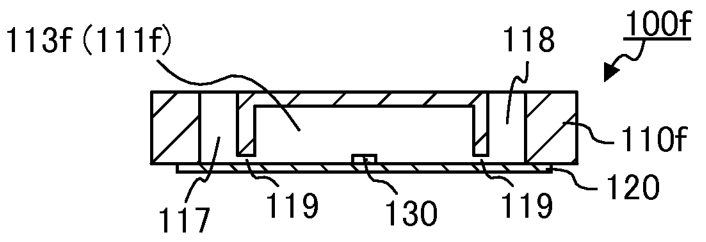

FIG. 8A is a plan view of microchip **100*f* according to a sixth modification of Embodiment 1, FIG. 8B is a sectional view taken along line B-B illustrated in FIG. 8A, and FIG. 8C is a sectional view taken along line C-C illustrated in FIG. 8A. As illustrated in FIGS. 8A to 8C, substrate 110*f* has recess 111*f* in place of first through-hole 111. First area 121 of film 120 closes the opening of recess 111*f* to thereby form housing part 113*f* capable of housing liquid. In addition, substrate 110*f* further includes two third through-holes and two grooves. First area 121 of film 120 closes the openings of the two third through-holes to form injection port 117 for introducing liquid into housing part 113*f* and ejection port 118. Further, first area 121 of film 120 closes the openings of two grooves to thereby form channel 119 in which liquid flows. Each one end of two channels 119 is in communication with housing part 113*f*, and each of the other ends of two channels 119 is in communication with injection port 117 or ejection port 118. Thus, it becomes possible to introduce liquid into housing part 113*f*** from the outside.

Embodiment 2

In Embodiment 2, microchannel chip 200 will be described that includes channel 217 in which liquid can move by capillary action and that enables voltage to be applied to a reagent and a liquid sample.

Microchannel chip 200 according to Embodiment 2 differs from microchip 100 according to Embodiment 1 in substrate 210 and conductive layer 230. Therefore, the same reference signs are allotted to the same components as those of microchannel chip 100 according to Embodiment 1, and the descriptions therefor will be omitted; components different from substrate 110 and conductive layer 130 of microchip 100 will be mainly described.

(Configuration of Microchannel Chip)

Figure 9A:
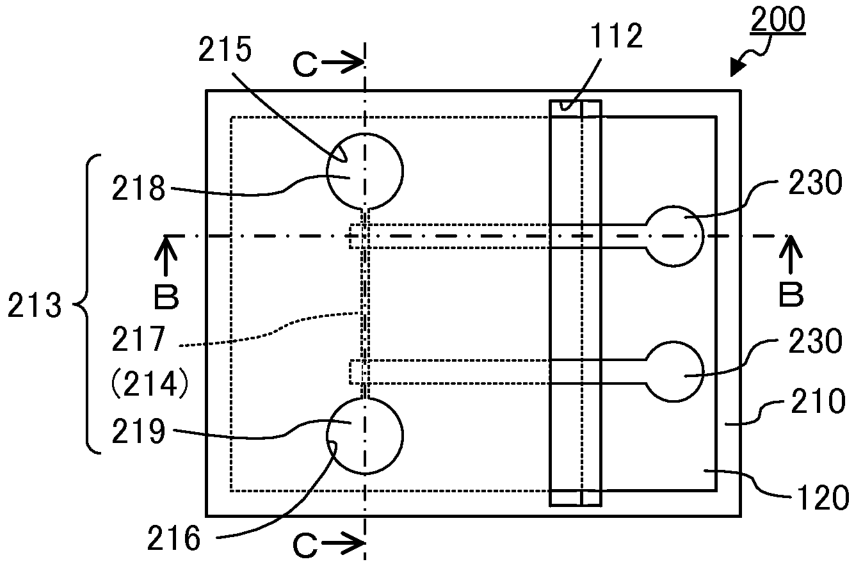
FIGS. 9A to 9C illustrate a configuration of a microchannel chip according to Embodiment 2.
Figure 9B:
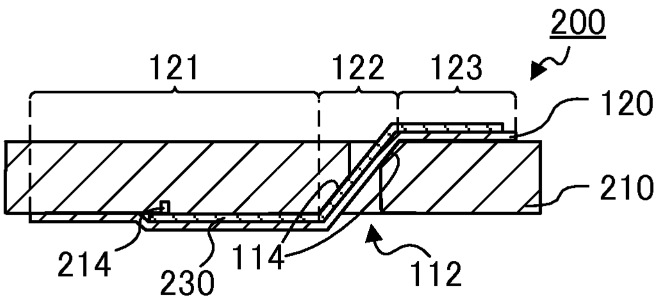
Figure 9C:
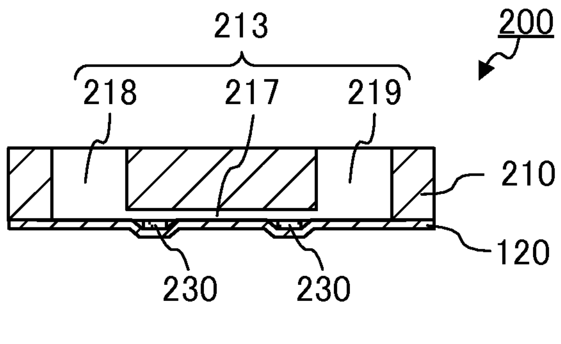

FIGS. 9A to 9C illustrate a configuration of microchannel chip 200 according to Embodiment 2. FIG. 9A is a plan view of microchannel chip 200, FIG. 9B is a sectional view taken along line B-B illustrated in FIG. 9A, and FIG. 9C is a sectional view taken along line C-C illustrated in FIG. 9A.

As illustrated in FIGS. 9A to 9C, microchannel chip 200 includes substrate 210, film 120, and two conductive layers 230.

Substrate 210 is a transparent substantially rectangular member. Substrate 210 includes groove (recess) 214, second through-hole 112, fourth through-hole 215, and fifth through-hole 216. Groove 214 opens at one surface (rear surface) of substrate 210. The opening of groove 214 is closed by film 120 to allow groove 214 to function as channel 217 in which liquid flows. The shape of groove 214 in cross-section orthogonal to the flowing direction of groove 214 is not particularly limited and is, for example, substantially rectangular with a length of one side (width and depth) of about several tens of μm.

Each of second through-hole 112, fourth through-hole 215 and fifth through-hole 216 opens at both surfaces of substrate 210. Fourth through-hole 215 is in communication with one end portion of groove 214. In addition, fifth through-hole 216 is in communication with the other end portion of groove 214. The shape of fourth through-hole 215 and fifth through-hole 216 is not particularly limited and is, for example, substantially columnar. The size of fourth through-hole 215 and fifth through-hole 216 either may be the same or different. The diameter of fourth through-hole 215 and fifth through-hole 216 is not particularly limited and is, for example, about 0.1 to 3 mm. The shape and size of second through-hole 112 are similar to those in Embodiment 1, and thus the descriptions therefor will be omitted.

The size and thickness of substrate 210, and the material for substrate 210 are also similar to those of substrate 110 according to Embodiment 1, and thus the descriptions therefor will be omitted.

In the present embodiment, film 120 closes the openings of groove 214, fourth through-hole 215 and fifth through-hole 216 of substrate 210 to form housing part 213 including channel 217, first recess 218 and second recess 219. Specifically, the opening of groove 214 is closed by film 120 to form channel 217 in which liquid can move by capillary action. In addition, the openings, on the side of the opening of groove 214, of fourth through-hole 215 and fifth through-hole 216 of substrate 210 are closed by film 120 to form first recess 218 and second recess 219. First recess 218 and second recess 219 are in communication with each other through channel 217.

As illustrated in FIGS. 9A to 9C, two conductive layers 230 are thermally or electrically conductive layers disposed on one surface of film 120 to extend in first area 121, second area 122 and third area 123. Each of conductive layers 230 disposed on first area 121 of film 120 is disposed on one surface side (rear surface) of substrate 210 such that a part of conductive layer 230 is exposed to the inside of channel 217. Each of conductive layers 230 disposed on third area 123 of film 120 is disposed on the other surface side (front side) of substrate 210 such that a part of conductive layer 230 is exposed to the outside. The material, thickness and application of conductive layer 230 are similar to those in Embodiment 1, and thus the descriptions therefor will be omitted.

In microchannel chip 200 according to the present embodiment, conductive layer 230 is connected to an external power source via an electrode connector (not illustrated). Voltage is applied between two conductive layers 230 with a liquid sample being present inside channel 217 to thereby enable voltage to be applied to the liquid sample inside channel 217. Also in the present embodiment, conductive layer 230 is disposed on substrate 210 through film 120, and thus can be connected to the electrode connector with a sufficient contact pressure. In addition, since conductive layer 230 and the electrode connector can be thus connected to each other at a position inward from the outer edge of substrate 210, microchannel chip 200 can be reduced in size.

(Effect)

As described above, also in microchannel chip 200 according to Embodiment 2, it is possible to dispose conductive layer 230 on both sides of substrate 210 through second through-hole 112. Thus, an electrode connector and conductive layer 230 can contact each other on substrate 210 in a stable state. Therefore, conductive layer 230 and the electrode connector may be connected to each other with a sufficient contact pressure. Microchannel chip 200 according to Embodiment 2 can be properly installed for example in a measurement device having an insertion type connector, to thereby enable precise measurement, processing, or the like to be performed for smaller amounts of materials.

It is noted that while conductive layer 230 is used as an electrode for applying voltage in microchannel chip 200 according to Embodiment 2, the application of the conductive layer is not limited to the electrode for applying voltage. In addition, also in microchannel chip 200 according to Embodiment 2, a recess may be formed at the other surface of substrate 210, for housing the end portion in third area 123 of film 120 (see FIGS. 7A and 7B).

While Embodiment 2 is directed to microchannel chip 200 having channel 217 in which liquid can move by capillary action, it is also possible to employ microchannel chip 200 having channel 217 in which liquid can move by other means not utilizing capillary action (e.g., pump). In this case, the size of a cross-section of channel 217 (groove 214) may be set more freely.

While Embodiments 1 and 2 are directed to microchip 100 and microchannel chip 200 for processing, analysis or the like of a liquid sample, the fluid handling device according to the present invention may also be used for processing, analysis or the like of fluids other than liquids (such as mixture, slurry, and suspension).

INDUSTRIAL APPLICABILITY

The fluid handling device of the present invention is advantageous as a microchip or a microchannel chip to be used for example to analyze smaller amounts of materials in the fields of science and medicine.

REFERENCE SIGNS LIST

10 Microchannel chip
14 Microchannel (Channel)
18 Substrate
20 Plate
26 Reservoir
28 Electrically conductive layer
100, 100*c*, 200 Microchip (Microchannel chip)

110, 110*a*, 110*b*, 110*c*, 110*d*, 110*e*, 110*f*, 210 Substrate
111 First through-hole
111*f* recess
112, 112*a*, 112*b* Second through-hole
113, 113*f*, 213 Housing part
114, 114*a* Inclining surface
115 Liquid
116*c* Reinforcing part
116*d*, 116*e* Recess
117 Injection port 118 Ejection port
119 Channel
120 Film
121 First area
122 Second area
123 Third area
130, 230 Conductive layer
135 Heater
214 Grove (recess)
215 Fourth through-hole
216 Fifth through-hole
217 Channel
218 First recess
219 Second recess

The invention claimed is:

1. A fluid handling device comprising:

a substrate including a first through-hole or a recess, and a second through-hole;

a film including a first area, a second area disposed adjacent to the first area, and a third area disposed adjacent to the second area; and a conductive layer disposed on one surface of the film to extend in the first area, the second area and the third area to conduct electricity or heat, wherein:

the substrate includes a first surface and a second surface facing away from the first surface, the first area of the film is bonded to the first surface of the substrate such that a housing part capable of housing liquid is formed by closing one opening of the first through-hole or an opening of the recess, and such that a part of the conductive layer is exposed to an inside of the housing part, the second area of the film is disposed inside the second through-hole, and the third area of the film is bonded to the second surface of the substrate such that a part of the conductive layer is exposed to an outside.

2. The fluid handling device according to claim 1, wherein an inclining surface is formed, in at least one opening of the second through-hole, to be away from the housing part as being away from the first surface toward the second surface of the substrate.

3. The fluid handling device according to claim 1, wherein a recess is formed at the second surface of the substrate, and an end portion in the third area of the film is housed in the recess.

4. The fluid handling device according to claim 1, wherein the substrate has a reinforcing part at a position facing an end portion of the film inside the second through-hole.

5. The fluid handling device according to claim 1, wherein the housing part has a channel in which liquid can move by capillary action.

6. The fluid handling device according to claim 1, wherein the conductive layer is a thin metal film or a conductive ink layer.

* * * * *